US008162140B2

(12) United States Patent
Hansen et al.

(10) Patent No.: US 8,162,140 B2
(45) Date of Patent: Apr. 24, 2012

(54) SPECIMEN RETENTION CONTAINER (75) Inventors: John G. Hansen, Moneta, VA (US); C. Alan Henry, Roanoke, VA (US)

(73) Assignee: 2 View, LLC, Moneta, VA (US)

( * ) Notice: Subject to any disclaimer, the term of this patent is extended or adjusted under 35 U.S.C. 154(b) by 600 days.

(21) Appl. No.: 11/697,464

(22) Filed: Apr. 6, 2007

(65) Prior Publication Data
US 2007/0237684 A1 Oct. 11, 2007

Related U.S. Application Data

(60) Provisional application No. 60/789,668, filed on Apr. 6, 2006.

(51) Int. Cl.
*A61B 17/06* (2006.01)
(52) U.S. Cl. .......... 206/438; 422/400; 600/562
(58) Field of Classification Search .......... 422/102; 206/204
See application file for complete search history.

(56) References Cited

U.S. PATENT DOCUMENTS

| | | | |
|---|---|---|---|
| 3,140,007 A * | 7/1964 | Nettleship | 206/508 |
| 3,332,316 A | 7/1967 | Saunders | |
| 3,378,684 A | 4/1968 | Mentink et al. | |
| 3,462,598 A | 8/1969 | Burke et al. | |
| 3,498,724 A | 3/1970 | Hayes et al. | |
| 3,554,433 A | 1/1971 | Cardenaz | |
| D222,352 S | 10/1971 | Ferro et al. | |
| 4,037,109 A | 7/1977 | Hosokawa et al. | |
| 4,115,689 A | 9/1978 | Won | |
| 4,409,854 A | 10/1983 | Solazzi | |
| 4,448,311 A | 5/1984 | Houser | |
| 4,974,244 A * | 11/1990 | Torrisi et al. | 378/45 |
| 5,040,678 A * | 8/1991 | Lenmark et al. | 206/443 |
| 5,077,218 A * | 12/1991 | Marquette et al. | 435/284.1 |
| 5,160,021 A * | 11/1992 | Sibley et al. | 206/204 |
| 5,315,147 A * | 5/1994 | Solomon | 257/448 |
| 5,316,147 A * | 5/1994 | Weber-Unger | 206/438 |
| 5,323,441 A | 6/1994 | Torrisi et al. | |

(Continued)

FOREIGN PATENT DOCUMENTS
WO WO 95/14221 5/1995

OTHER PUBLICATIONS

Specimen Radiography Devices from Cone Instruments, http://www.coneinstruments.com/CIcatsub1.asp?cat_id=1317, one page, Feb. 4, 2006.

(Continued)

*Primary Examiner* — Max Hindenburg
*Assistant Examiner* — Renee Danega
(74) *Attorney, Agent, or Firm* — Charles S. Sara, Esq.; Daniel A. Blasiole; DeWitt Ross & Stevens, S.C.

(57) ABSTRACT

A container and method of using the container to maintain an excised tissue specimen in a fixed orientation during transport and imaging is described. The container includes a body, a flexible, soft retainer capable of holding various sized specimens, an adjustable soft retainer that interacts with the body to retain the specimen against the soft retainer without significant compression or distortion, and a lid that snaps tightly to the body reducing bodily fluid leakage when the container is placed in a horizontal position, and preventing contamination of the specimen.

24 Claims, 6 Drawing Sheets

U.S. PATENT DOCUMENTS

| | | | |
|---|---|---|---|
| 5,383,234 A | 1/1995 | Russell | |
| 5,383,472 A | 1/1995 | Devlin et al. | |
| 5,427,742 A | 6/1995 | Holland | |
| 5,609,827 A * | 3/1997 | Russell et al. | 422/102 |
| D380,555 S | 7/1997 | Kurosaki et al. | |
| D382,063 S | 8/1997 | Stevens et al. | |
| D383,851 S | 9/1997 | Wong | |
| 5,976,895 A | 11/1999 | Cipkowski | |
| 5,996,798 A * | 12/1999 | Gessert | 206/521 |
| 6,085,909 A * | 7/2000 | Lyons | 206/584 |
| 6,128,889 A * | 10/2000 | Fuss | 53/472 |
| 6,225,107 B1 | 5/2001 | Nagle | |
| 6,603,544 B1 | 8/2003 | Eckert | |
| 7,022,289 B1 | 4/2006 | Schlein et al. | |
| 2002/0141904 A1* | 10/2002 | Rosen et al. | 422/102 |
| 2003/0013589 A1 | 1/2003 | Tsukui et al. | |
| 2005/0000841 A1* | 1/2005 | DuBois et al. | 206/438 |

OTHER PUBLICATIONS

US 5,787,597 A1, 11/1989, Haast, (withdrawn).

* cited by examiner

SPECIMEN RETENTION CONTAINER

REFERENCE TO RELATED APPLICATION

The application claims priority to U.S. Provisional Application entitled "Specimen Retention Device," Ser. No. 60/789,668, filed Apr. 6, 2006, which is incorporated herein by reference in its entirety.

FIELD OF THE INVENTION

The invention relates to a container to maintain an excised tissue specimen such as an excisional biopsy or partial mastectomy excision in a stable orientation throughout subsequent imaging and transport.

DESCRIPTION OF THE PRIOR ART

When a patient is diagnosed with a tissue abnormality and undergoes a surgical procedure for its removal, there are times when it is advisable to take radiographic views of the resected tissue specimen to assess the adequacy of the resection. As used in the present invention, the term "tissue specimen" may refer to a wide variety of animal tissue specimens. Examples include breast tissue and brain or other organ tissue. The term "tissue specimen" can also refer to vegetable tissues. As the present invention has application in many common pathologic scenarios, for simplicity its application to breast tissue specimen biopsies will be described.

In evaluating this removed specimen it is useful for the surgeon to see mammographic images of the specimen in an undisturbed condition and in two different planes to ensure that the area of interest is fully contained inside the specimen. If the two images indicate that the specimen fully contains the area of interest, the surgeon can be confident that it has been fully removed and the patient will not have to undergo re-excision. If the two images indicate that the area of interest is too close to the margins of the specimen, the surgeon can remove more material before finalizing the surgery, thereby preventing a return to the operating room for re-excision at a later date.

A variety of devices are available for securing and transporting such excised tissue for pathologic and/or radiologic evaluation. For example, tissue specimens can be compressed between two plates in a container. However, this type of device creates distortion of the specimen rendering accurate margin analysis nearly impossible. It also does not allow for radiologic evaluation in multiple planes unless the specimen is removed and reoriented, which disturbs the specimen enough to render the images inaccurate. There is also an invention that is rectangular in shape and would allow for multiple plane radiologic analysis (U.S. Pat. No. 6,225,107 to Nagle). However, this device attempts to reshape the specimen into a rectangular space creating some degree of distortion. It also fails to prevent the leakage of body fluids thereby exposing the handlers to potential blood borne pathogens.

SUMMARY OF THE INVENTION

The present invention is directed to a tissue specimen container for analyzing a tissue specimen, comprising a closeable container including a body and a lid, and further comprising an interior chamber between the lid and the body when the container is in a closed position; wherein the lid comprises a top surface and a first edge; wherein the body comprises a top surface having a second edge and a bottom surface, wherein the bottom surface is defined by a specimen-containing concave depression; and wherein the interior chamber is adapted to contain the specimen between and in contact with the lid and the body in a known, fixed orientation with minimal compression, minimal movement, and minimal fluid leakage.

The present invention is further directed to a tissue specimen container for analyzing a tissue specimen, comprising a closeable container including a body and a lid, and further comprising an interior chamber between the lid and the body when the container is in a closed position; wherein the lid comprises a top surface and a first edge; wherein the body comprises a top surface having a second edge and a bottom surface, wherein the bottom surface is defined by a specimen-containing concave depression; wherein the interior chamber is adapted to contain the specimen between and in contact with the lid and the body in a known, fixed orientation with minimal compression, minimal movement, and minimal fluid leakage; wherein the container comprises either a transparent or a translucent material for radiographic imaging; and wherein the first edge of the lid is adapted to be sealingly engaged with the second edge of the body to form a leak-proof seal; and at least one retainer formed of a soft flexible radiographically-transparent material to facilitate the retention of the specimen within the container.

The present invention is further directed to a method of handling a tissue specimen comprising the following steps: a) placing the specimen inside a tissue specimen container, comprising a closeable container including a body and a lid, and further comprising an interior chamber between the lid and the body when the container is in a closed position; wherein the lid comprises a top surface and a first edge; wherein the body comprises a first radiographically-viewing surface having a second edge, a second radiographically-viewing surface, and a bottom surface, wherein the bottom surface is defined by a specimen-containing depression; and wherein the interior chamber is adapted to contain the specimen between and in contact with the lid and the body in a known, fixed orientation with minimal compression, minimal movement, and minimal fluid leakage; b) closing the lid onto the body such that the specimen is immobilized in the interior of the container; c) placing the container in a first position to produce an x-ray image of the specimen through the first radiographically-viewing surface; and d) placing the container in a second position to produce an x-ray image of the specimen through the second radiographically-viewing surface.

The tissue specimen container is especially suited to cradle an excised tissue specimen in a secure position without using deforming pressure. Because the tissue specimen can be gently held in a fixed position in the tissue specimen container, the container can be placed in a number of positions without risk of deforming or shifting the specimen. This feature is especially important when taking x-rays along different axes of the excised specimen. The tissue specimen container allows a physician to accurately maintain the natural shape of the excised specimen, relative to the area of interest, and determine if the excision of the tissue specimen was effective.

The tissue specimen container may also be used to hold the specimen during transport and radiographic imaging. The tissue specimen container allows for radiographic imaging of the specimen in multiple planes without the need for handling the specimen or opening the container. The tissue specimen container ensures that when the specimen is received for pathological assessment, it has not been handled or exposed to potential contaminants since being placed in the container by the surgical staff.

The container further reduces the likelihood that medical staff will be exposed to potentially hazardous bodily fluids.

The present invention has many advantages over prior specimen retention containers. The present invention is easy to use and reduces distortion of the tissue specimen during handling and imaging. The substantially-concave floor of the tissue specimen container allows a generally amorphous, but often spheroid tissue specimen to rest in the tissue specimen container without encountering any sharp corners or flat surfaces. By gently cradling the tissue specimen, the substantially-concave floor does not distort the lower surface of the specimen.

The addition of a soft lower retainer placed in the substantially-concave floor adds another level of security to the tissue specimen. The soft lower retainer further softens any pressure to the specimen from the floor of the container. In addition, the lower retainer lifts the specimen above the place where the floor meets the walls, an area that could cause distortion in imaging. The soft upper retainer, which is placed on top of the specimen, gently holds the specimen in place within the tissue specimen container. This is accomplished without exerting any distortional force onto the specimen. Therefore, with the specimen secured within a fixed position, X-rays or other radiographs can be taken while maintaining the specimen's structural integrity and relative frame of reference.

Because a tissue specimen's structural integrity is not deformed during imaging, the physician can accurately gauge the spatial location of any specific or notable locations within the specimen. The unique design of the present invention and the method for its use gives physicians a significant tool in their repertoire for treating patients.

Furthermore, the locking lid helps reduce the leakage of any body fluids associated with the specimen.

The objects and advantages of the invention will appear more fully from the following detailed description of the preferred embodiment of the invention made in conjunction with the accompanying drawings.

DETAILED DESCRIPTION OF THE INVENTION

Figure 1:
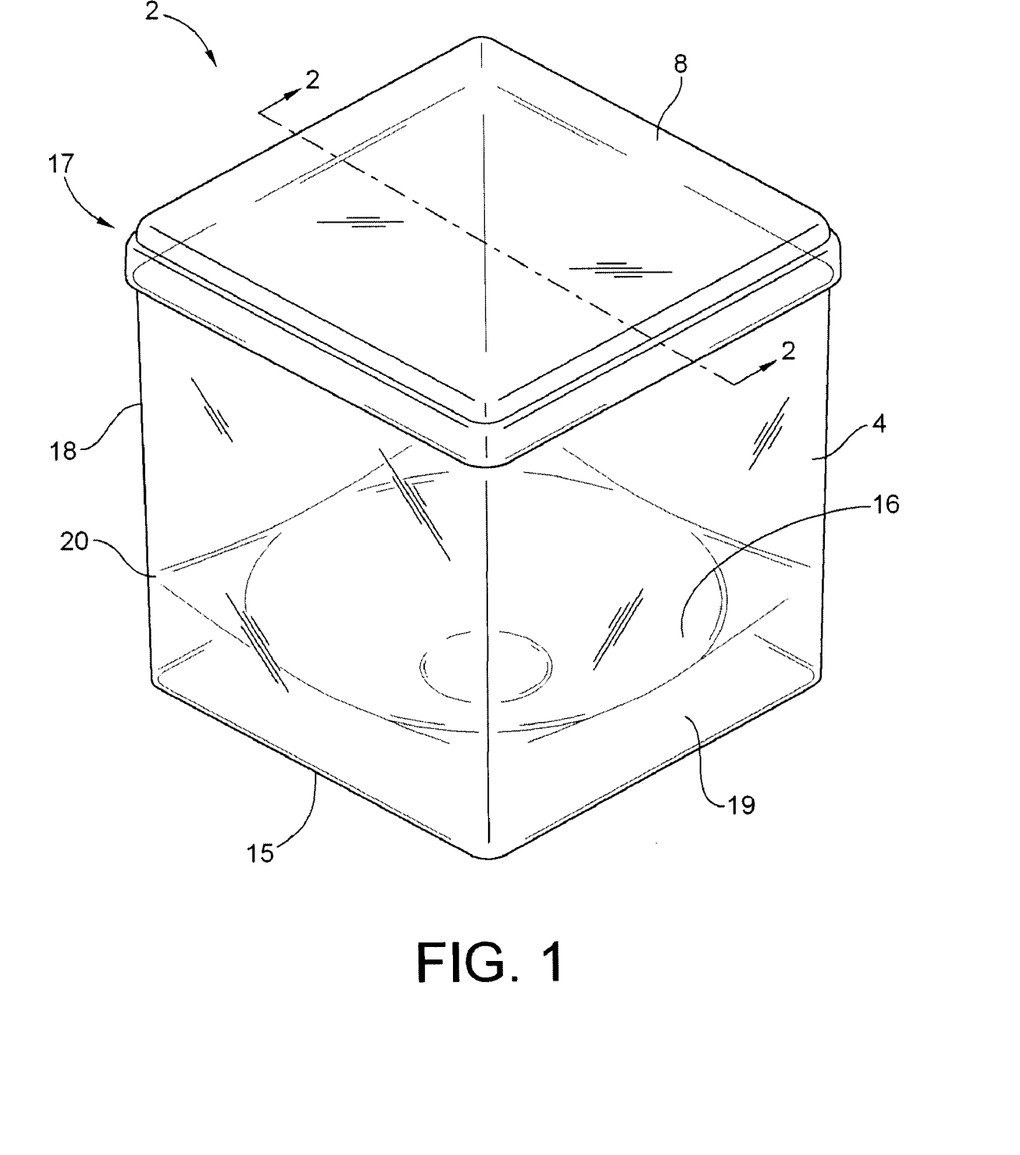
FIG. 1 is a perspective view of the specimen retention container of the present invention.
Figure 2:
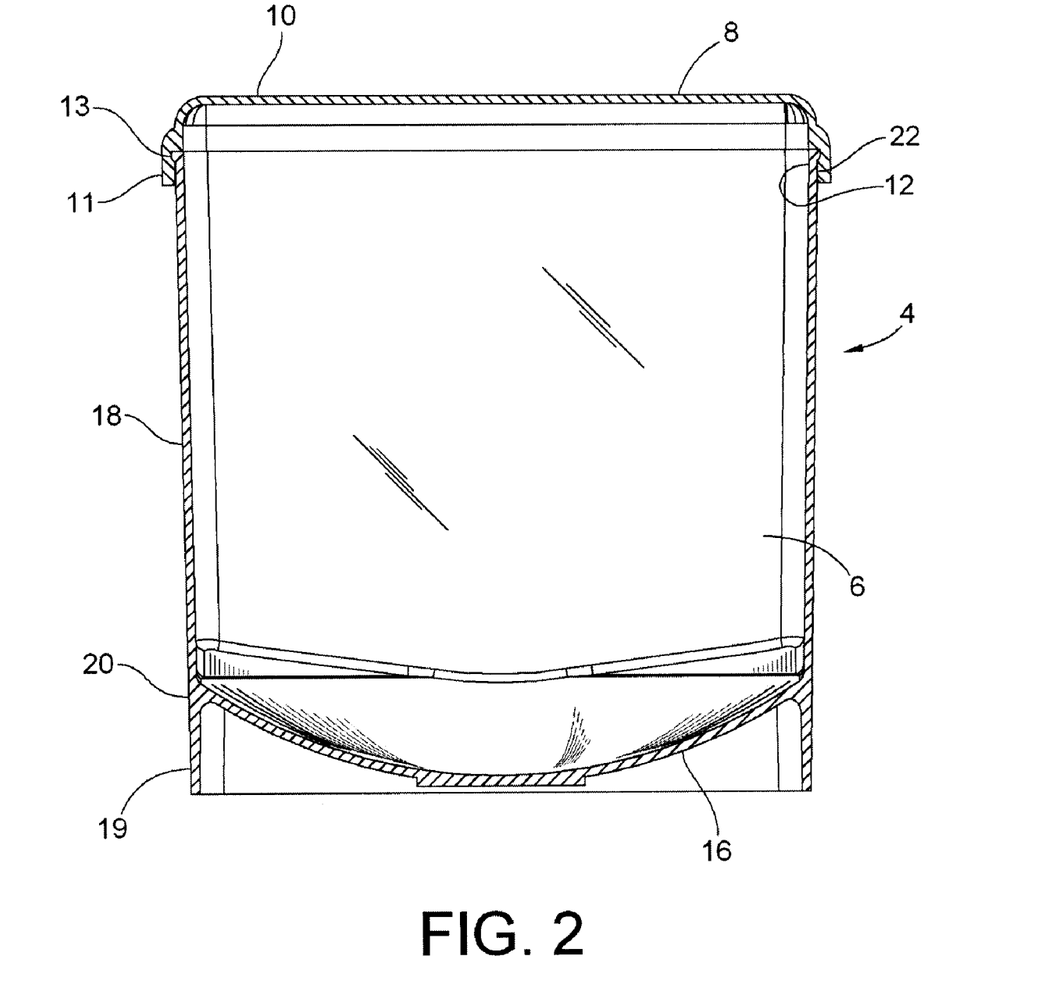
FIG. 2 is a perspective cross-section view of the specimen retention container of FIG. 1 taken along line 2-2 of FIG. 1.
Figure 3:
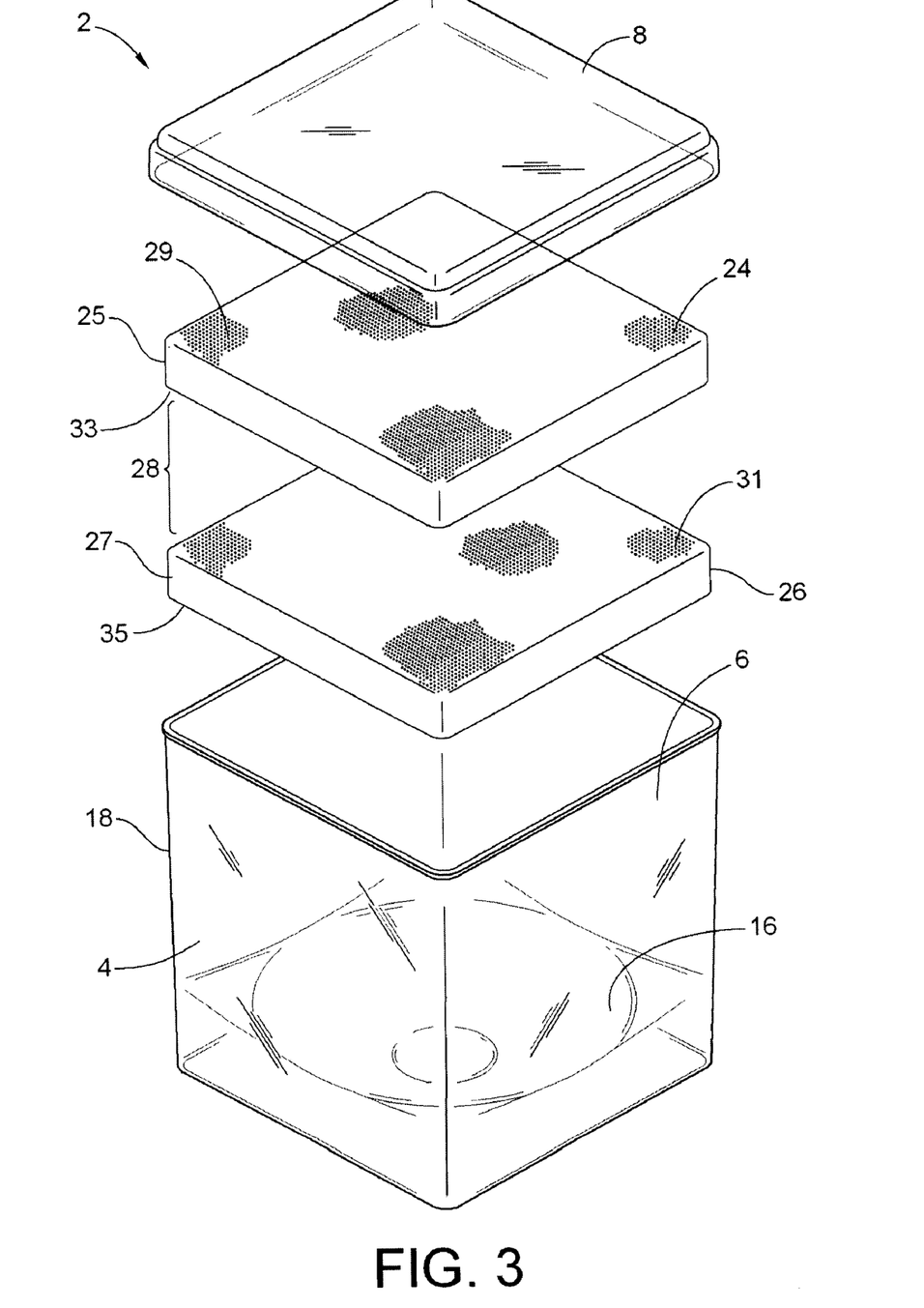
FIG. 3 is an exploded perspective view of the container of FIG. 1.

Referring now to the drawings, FIGS. 1-3 illustrate an assembled view of the components of the specimen retention container 2, which includes a body 4 and a separate lid 8.

The body 4 is generally boxed-shaped and includes four substantially parallel walls 18 defining an interior 6 of the body 4, a lower end 15 and an open upper end 17. The lower end 15 is defined by a substantially-concave floor 16, which is positioned opposite of the open end 17 and effectively forms an impermeable closed lower end 15. The concave floor 16 is joined to the outer walls 18 at junction 20 at variable positions distant from the open end 17. The upper open end 17 of the container is defined by a lip 2 which extends outwardly from the walls 18 for mating engagement with the lid 8.

As illustrated in FIG. 1, the junction 20 forms the upper edge of the substantially-concave floor 16. In this configuration, the lower end 15 of the container 2 can sit on a flat surface or plane, parallel and opposite the lid 8. While the outer walls 18 are preferably dimensioned as a square creating a container 2 with a cube-shape, it is within the scope of the present invention to shape the outer walls into a round cylinder, a triangle or other polygon shape (not shown). As illustrated, the junction 20 of the substantially-concave floor 16 and the outer walls 18 is located nearer the lower end 15 of the body 4. However, it is within the scope of the present invention to place the junction 20 at other locations along the walls 20 closer to the open end 17 if desired. The arc of the substantially-concave floor 16 is variable as long as it still creates a resting place for the tissue specimen.

The lid 8 can be of any reasonable shape as long is it is adapted to securely fit on the open end 17 of the container 2. As illustrated in FIG. 2, the lid 8 is defined by an upper surface 10, and walls 11. The walls 11 are designed to fit in mating engagement over the walls 18 of the body 4 at upper end 17. The walls 11 include an inner surface 12 which are defined by an indent 13. The purpose of the indent 13 is to releasibly secure the lip 22 of the body in order to snap fit the lid 8 onto the body preferably in a seal tight fashion to prevent any liquid flowing in or out of the container when the lid 8 is engaged with the body 4. Although a snap or lock mechanism is illustrated, it is within the scope of the present invention to secure the lid 8 using a screw or twist mechanism or other variations of an interactive fit.

The entire container 2 is made of a transparent or a translucent material for radiographic imaging. The container 2 is preferably constructed of a radiographically-transparent material, which has the characteristics of an optically-clear radiographically-transparent material so that the physician can visualize the placement of the specimen. Materials suitable for fabrication of the container 2 include glass, and synthetic polymers such as acrylics, polycarbonates, polyolefins, polyurethanes, polystyrenes and the like. A suitable polystyrene is commercially available from Dow Plastics (Midland, Mich.) under the trademark "Styron 666".

Referring now to FIG. 3, there is illustrated an exploded view of a fully assembled specimen retention container 2. The order of assembly of the completed specimen retention container 2 is implicitly shown with the optional addition of an upper soft retainer 24 and a lower soft retainer 26. The retainers 24 and 26 are preferably made of any soft and flexible material that is radiographically-transparent including soft rubber or foam polymers. The retainers 24 and 26 are generally shaped into the same configuration as the interior 6 of the body 4 and designed to fit within the interior 6 of the body 4 in a snug fit manner such that the walls 25 and 27 of each retainer 24, 26 are press fit against the interior of the walls 18 of the body 4. While the retainers 24 and 26 are illustrated in a rhomboid shape having four generally identical side walls 25 and 27, an upper surface 29 and 31, and a lower surface 33 and 35, respectively, it is within the scope of the present invention to provide retainers in any shape or form as long as the retainers 24 and 26 serve the primary purpose of engaging the tissue specimen within the container 2 in such manner to prevent movement of the specimen during analysis while also maintaining the proper shape of the tissue specimen. The surface of the retainers may be smooth, as illustrated in the figures, or convoluted, such as an egg-shell foam shape. Non-limiting examples of materials suitable for use include low-density blown polymers and open-cell polymer foams made from acrylics, polycarbonates, polyolefins, polyurethanes, polystyrenes and the like. A suitable polystyrene is commercially available from Dow Plastics (Midland, Mich.) under the trademark "Voralux HL 430".

Figure 4:
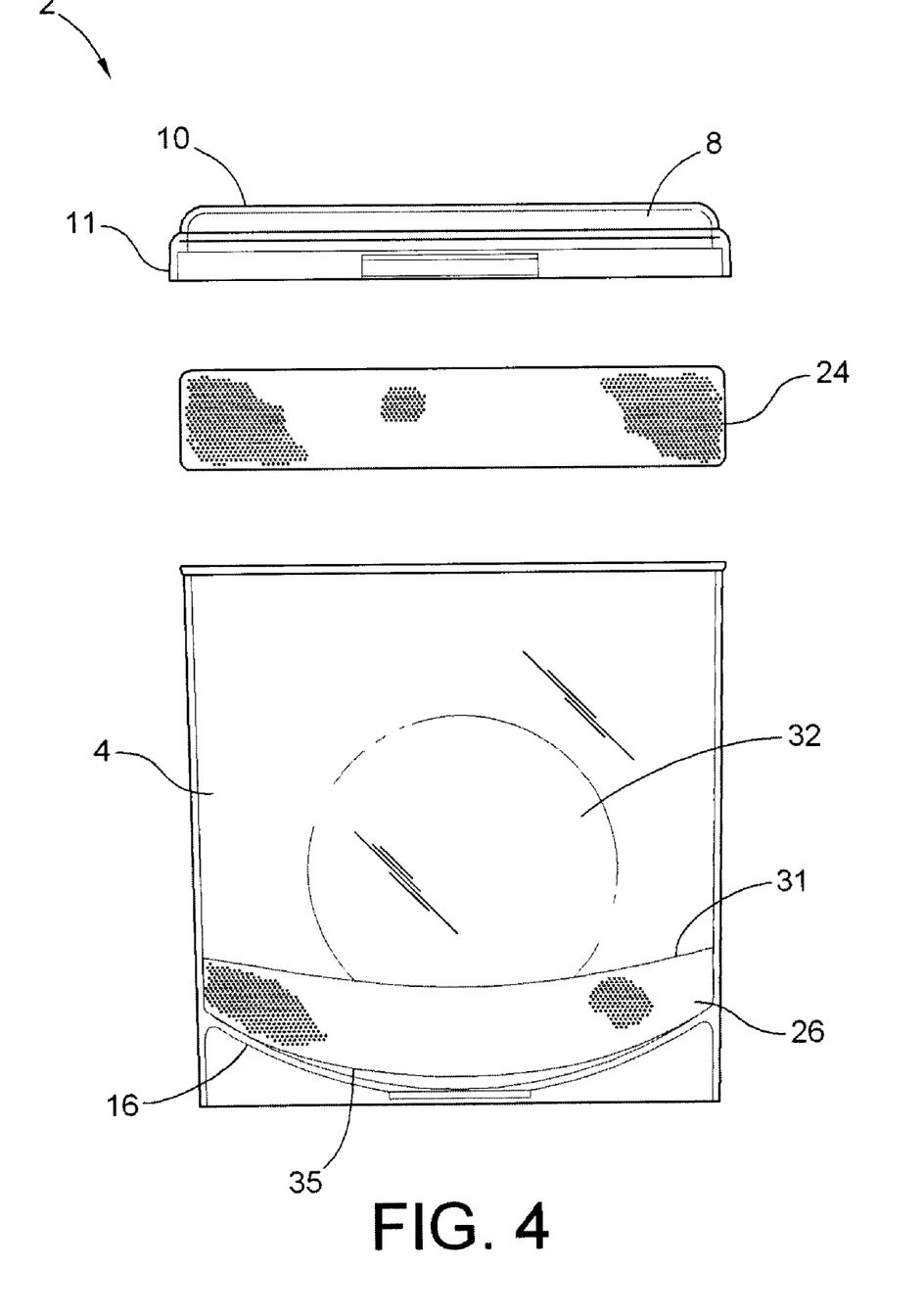
FIG. 4 is a side plan and exploded view of the container of FIG. 1.

In operation, the lower soft retainer 26 is placed into the body 4 of the container 2. The lower soft retainer is gently seated into the concave floor 16 as illustrated in FIG. 4, such that the lower surface 35 is adjacent the concave floor 16 and remains fixed in place due to the snug fit meeting of the wall 27 with the interior surface of the continuous outer wall 18. The interference fit results from the lower soft retainer being slightly wider than the inside of the body 4 of the container 2. As illustrated in FIG. 4, the upper surface 31 of the retainer 26 forms a concave bowl-like shape due to the press fit relationship of the retainer 26 on the concave floor 16. The retainer 26 also serves the function of placing the specimen 32 above junction 20 in the walls 18 such that no part image of the specimen 32 will be distorted by the line in the wall 18 caused by the junction 20.

Figure 5:
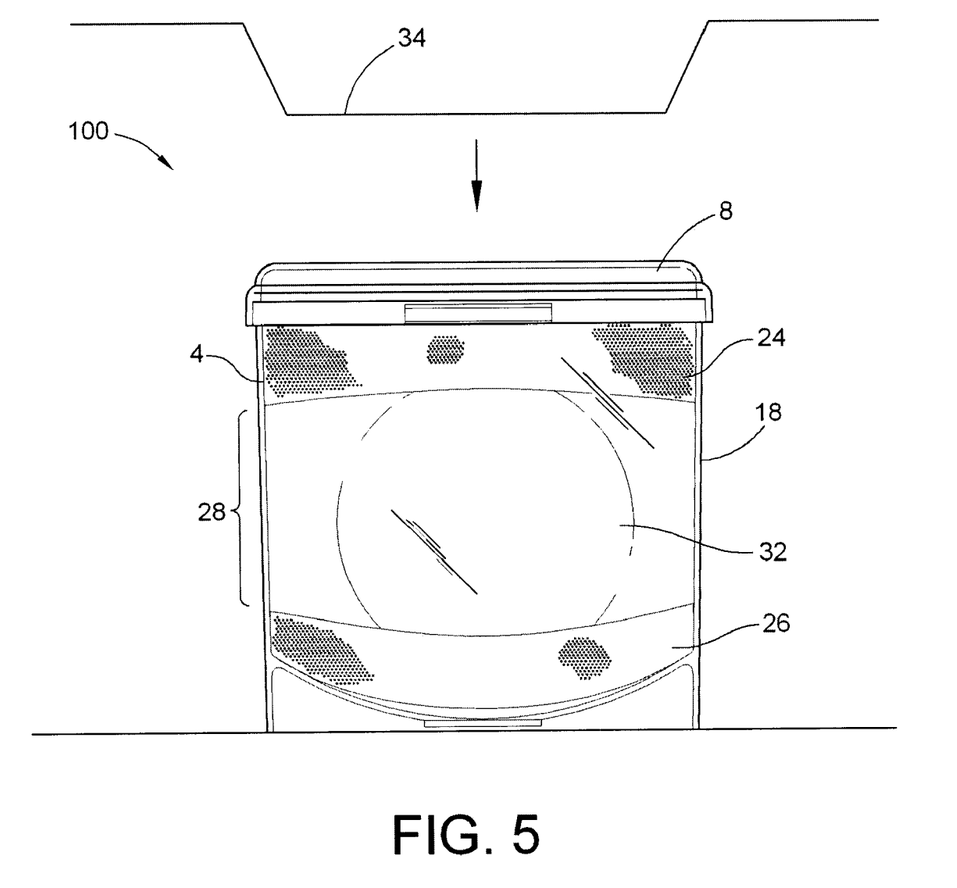
FIG. 5 is a side plan view illustrating the assembled specimen retention container of FIG. 4 in a first position relative to an X-ray source.

The tissue specimen 32, typically an amorphous tissue mass, is then placed on the upper surface 31 of the retainer 26 and is seated in the concave depression on the retainer 26. The upper soft retainer 24 is gently placed into the body 4 of the container 2 and lowered into contact with the specimen 32 as illustrated in FIG. 5. Because the upper soft retainer 24 stays in place due to interference fit, only light pressure is required to keep the specimen 32 in place. Therefore, the specimen 32 is now seated in the container 2 without significant structural deformation. The lid 8 is then secured to the body 4 in a snap fit manner as discussed above.

When the lower soft retainer 26 and the upper soft retainer 24 are placed around the specimen 32 within the body 4, a specimen space 28 is created within the container 2. Because the lower soft retainer 26 and the upper soft retainer 24 are easily adjustable, yet remain in place, the specimen space 28 can be adjusted for different types and sizes of tissue specimens.

Although FIGS. 3-6 illustrate both a lower soft retainer 26 and an upper soft retainer 24, it is within the scope of the present invention to eliminate the use of either retainer 24 and 26 or to use only one retainer 24 or 26, depending on the size of the tissue specimen 32 or the purpose of the analysis. For example, a sufficiently large specimen may be placed directly onto the concave floor 16 and only require an upper soft retainer 24 to hold the specimen in place (not shown.)

FIG. 5 illustrates an assembled first view orientation 100 of the fully assembled specimen retention container 2 including a tissue specimen 32. When fully assembled, the container 2 is oriented in a first view 100 relative to an X-ray source 34. The x-ray image may be taken at this first orientation 100.

Figure 6:
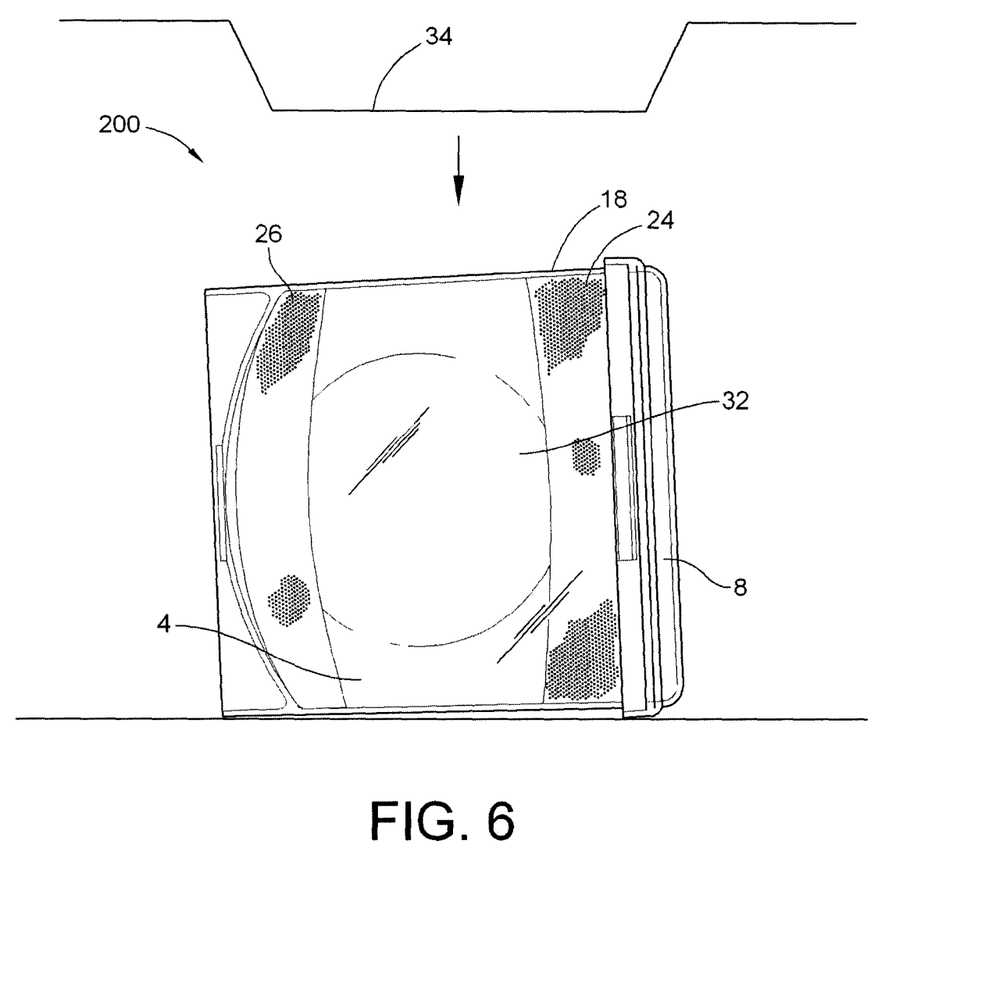
FIG. 6 is a side plan view illustrating the assembled specimen retention container of FIG. 4 in a second position relative to an X-ray source.

After the first orientation 100 is completed, the container 2 is turned onto its side, such that any of the walls 18 face the X-ray source 34, into a second view orientation 200 as illustrated in FIG. 6. As shown in FIG. 6, the assembled container 2, including the specimen 32, is gently placed on its side relative to the X-ray source 34. Because the lower soft retainer 26 and the upper soft retainer 24 securely fix the position of the specimen 32, the specimen 32 does not shift when placed into the second orientation 200. Furthermore, because the container 2 does not deform the specimen 32, the resultant X-ray images provide the physician with non-distorted views of the specimen. While FIG. 5 and FIG. 6 illustrate two views 100 and 200 of a specimen, more views may be taken. Furthermore, the container 2 can be constructed in different shapes, which may provide different axial views of the specimen 32.

Method of Use:

The excised specimen 32 is placed on the lower soft retainer 26 or directly onto the substantially-concave floor 16 of the body 4. The specimen 32 can be oriented in any position a physician desires. The specimen 32 may also be marked with margin orientation markers or ink. The upper soft retainer 24 is inserted into the body 4 by gently pushing it into the body 4 to overcome the interference fit. The upper soft retainer 24 is lowered against the specimen 32 to prevent movement without undue distortion. The upper soft retainer 24 is locked into position by inference fit with the body 4. The lid 8 is snapped into place over the lip 22 on the outer wall 18 adjacent to the open end 17 of the body 4. The locking lid 8 prevents specimen 32 contamination and exposure to bodily fluids.

The container 2 is used by first removing the container 2 from any packaging (not shown.) The container 2 is opened by removing the snap fit lid 8. Next, the upper soft retainer 24 is removed from the body 4. The specimen 32 is inserted into the substantially-concave floor 16 either directly or on top of the lower soft retainer 26. This should be done under the direction of the surgeon to ensure proper orientation and handling. The container 2 is placed on a flat surface, so that it is resting on the extensions 19. The upper soft retainer 24 is pressed gently into the body 4 in order to overcome the interference fit. The upper soft retainer 24 is gently lowered to the point that it gently but securely contacts the specimen 32. The upper soft retainer 24 is released to check the strength of the interference fit to ensure the retainer 24 will not move. The lid 8 is placed on the container 2 and the assembled container is placed into an imaging device 34. A first view 100 is taken of the specimen 32. The container is placed in a second orientation 200 and a second view is taken. The container is returned to the first orientation 100 and transported to pathology, where the lid 8 and the upper soft retainer 24 are removed. The specimen 32 is removed and pathology is performed as normal. The container can then be discarded in an appropriate biohazard disposal container.

It is understood that the invention is not confined to the particular construction and arrangement of parts herein illustrated and described, but embraces such modified forms thereof as come within the scope of the following claims.

What is claimed is:

1. A tissue specimen container for analyzing a tissue, comprising:
  a closeable container including a body and a lid, and further comprising an interior chamber between the lid and the body when the container is in a closed position;
    wherein the lid comprises a top surface and a first edge;
    wherein the body comprises a top surface having a second edge, walls, and a bottom surface; and
    wherein the bottom surface is defined by a substantially concave depression; and
  lower and upper retainers configured and dimensioned to retain different types and sizes of tissue specimens within the chamber in a known, fixed orientation without substantially deforming the tissue specimens;
    wherein the lower retainer is configured to be positioned adjacent the bottom surface of the body, wherein a top surface of the lower retainer defines a shape that substantially assumes a shape of the bottom surface of the body when positioned adjacent the bottom surface of the body and a specimen is placed thereon;
    wherein the upper retainer has a width greater than a width of the interior chamber and is structured to provide an interference fit in the chamber wherein the interference fit comprises a press fit of sides of the retainer against interior portions of the walls, wherein the upper retainer is capable of being continuously moveable between the second edge and the bottom surface and being securely positioned at any of a plurality of possible positions therebetween by a securing mechanism consisting of the interference fit, wherein a gap between the lower retainer positioned adjacent the bottom surface of the body and the upper retainer forms a specimen space, wherein size of the specimen space is continuously adjustable by virtue of secure positioning of the upper retainer between the second edge and the lower retainer resulting from the interference fit, wherein the upper retainer is capable of exerting a continuously adjustable pressure on a specimen disposed between the upper retainer and the lower retainer by virtue of continuously adjustable positioning between the second edge and the lower retainer, and wherein the upper and lower retainers are removable from the closeable container.

2. The container of claim 1 wherein the container comprises either a transparent or a translucent material for radiographic imaging.

3. The container of claim 1 wherein the lower retainer and the upper retainer are formed of a soft flexible radiographically-transparent material.

4. The container of claim 1 wherein the first edge of the lid is adapted to be sealingly engaged with the second edge of the body to form a leak-proof seal.

5. The container of claim 1 wherein the body comprises extensions extending from a junction between an edge of the bottom surface and the walls of the container to at least a lowest portion of the substantially concave depression, wherein the junction and the lowest portion of the substantially concave depression are not in the same plane.

6. A tissue specimen container for analyzing a tissue specimen, comprising:

a. a closeable container including a body and a lid, and further comprising an interior chamber between the lid and the body when the container is in a closed position; wherein the lid comprises a top surface and a first edge; and wherein the body comprises a top surface having a second edge, walls, and a bottom surface, wherein the bottom surface is defined by a substantially concave depression; and b. a retainer formed of a soft flexible radiographically-transparent material to facilitate retention of a tissue specimen within the interior chamber in a known, fixed orientation without substantially deforming the tissue specimen, wherein the retainer has a width greater than a width of the interior chamber, is structured to provide an interference fit of the retainer in the chamber, and is removable from the closeable container, wherein the interference fit comprises a press fit of sides of the retainer against interior portions of the walls, wherein the retainer is capable of being continuously moveable between the second edge and the bottom surface and being securely positioned at any of a plurality of possible positions therebetween by a securing mechanism consisting of the interference fit, and wherein a gap between the bottom surface of the body and the retainer forms a specimen space, wherein size of the specimen space is continuously adjustable by virtue of secure positioning of the retainer between the second edge and the bottom surface of the body resulting from the interference fit.

7. The container of claim 6 further comprising a second retainer configured to be positioned adjacent the bottom surface of the body to facilitate retention of the specimen.

8. The container of claim 6 wherein the retainer is formed of a soft flexible radiographically-transparent material.

9. The container of claim 6 wherein the body comprises extensions extending from a junction between an edge of the bottom surface and the walls of the container to at least a lowest portion of the substantially concave depression, wherein the junction and the lowest portion of the substantially concave depression are not in the same plane.

10. The container of claim 6 wherein the retainer is capable of exerting a continuously adjustable pressure on a specimen disposed under the retainer by virtue of continuously adjustable positioning of the retainer.

11. The container of claim 6 wherein a gap under the retainer forms a specimen space, wherein size of the specimen space is continuously adjustable by virtue of continuously adjustable positioning of the retainer.

12. The container of claim 6 wherein the interference fit consists in a press fit of sides of the retainer against interior portions of the walls.

13. The container of claim 6 wherein the container comprises a radiographically-transparent material for radiographic imaging.

14. The container of claim 6 wherein the first edge of the lid is adapted to be sealingly engaged with the second edge of the body to form a leak-proof seal.

15. The container of claim 7 wherein when the second retainer is positioned adjacent the bottom surface of the body and a specimen is placed thereon, a top surface of the second retainer substantially assumes a shape of the bottom surface of the body.

16. A method of handling a tissue specimen with a tissue specimen container as recited in claim 6 comprising the steps of:

a. placing the specimen inside a tissue specimen container, comprising a closeable container including a body and a lid, and further comprising an interior chamber between the lid and the body when the container is in a closed position;

1. wherein the lid comprises a top surface and a first edge; and 2. wherein the body comprises a first radiographically-viewing surface having a second edge, and a bottom surface, wherein the bottom surface is defined by a substantially concave depression;

b. inserting a retainer into the interior chamber in contact with the specimen, wherein the retainer has a width greater than a width of the interior chamber, is removable from the closeable container, and is structured to provide an interference fit of the retainer in the interior chamber, the interference fit comprising a press fit against interior portions of walls of the body, wherein the retainer is capable of being continuously moveable between the second edge and the bottom surface and being securely positioned at any of a plurality possible positions therebetween by a securing mechanism consisting of the interference fit, and wherein the inserting the retainer includes pushing it into the interior chamber to overcome the interference fit until the retainer comes in contact with the specimen, wherein the retainer is secured against the specimen by virtue of the interference fit and the specimen is immobilized in the interior chamber in a known, fixed orientation without substantially deforming the tissue specimen;

c. closing the lid onto the body; and d. placing the container in a first position to produce an x-ray image of the specimen through the first radiographically-viewing surface.

17. The method of claim 16 comprising before step a., placing a lower retainer adjacent the bottom surface of the body to facilitate the retention of the specimen within the container.

18. The method of claim 16 wherein the retainer is formed of a soft flexible radiographically-transparent material.

19. The method of claim 16 wherein the closing the lid comprises sealingly engaging the first edge of the lid with the second edge of the body to form a leak-proof seal.

20. The method of claim 16 further comprising after step d., placing the container in a second position to produce an x-ray image of the specimen through a second radiographically-viewing surface.

21. The method of claim 16 wherein the retainer is capable of exerting a continuously adjustable pressure on a specimen disposed between the retainer and the bottom surface of the body by virtue of continuously adjustable positioning provided by the interference fit, wherein the specimen is a soft tissue specimen, and wherein the inserting the retainer further comprises lowering the retainer against the specimen to prevent movement of the specimen without distorting the specimen.

22. The method of claim 16 wherein a gap under the retainer forms a specimen space and a size of the specimen space is continuously adjustable by virtue of secure positioning of the retainer, and wherein the inserting the retainer further comprises lowering the retainer to reduce the specimen space until the retainer contacts the specimen and prevents movement of the specimen without distorting the specimen.

23. The method of claim 17 wherein the placing the lower retainer adjacent the bottom surface of the body induces a top surface of the lower retainer to substantially assume a shape of the bottom surface of the body, wherein the top surface of the lower retainer forms a substantially concave surface, and wherein the placing the specimen inside the tissue container further comprises placing the specimen in the substantially concave surface of the top surface of the retainer.

24. The method of claim 17 wherein the interference fit consists in a press fit of sides of the retainer against interior portions of the walls.

* * * * *